(12) United States Patent
Liu et al.

(10) Patent No.: US 12,408,832 B2
(45) Date of Patent: Sep. 9, 2025

(54) VISION-TESTING METHOD AND DEVICE THEREOF

(71) Applicant: Wei Liu, Shenzhen (CN)

(72) Inventors: Wei Liu, Shenzhen (CN); Junlong Liu, Shenzhen (CN); Juntao Liu, Shenzhen (CN); Junchao Liu, Shenzhen (CN); Junshuai Liu, Shenzhen (CN)

( * ) Notice: Subject to any disclaimer, the term of this patent is extended or adjusted under 35 U.S.C. 154(b) by 835 days.

(21) Appl. No.: 17/621,681

(22) PCT Filed: Jul. 30, 2020

(86) PCT No.: PCT/CN2020/105657
§ 371 (c)(1),
(2) Date: Dec. 21, 2021

(87) PCT Pub. No.: WO2021/018224
PCT Pub. Date: Feb. 4, 2021

(65) Prior Publication Data
US 2022/0354361 A1    Nov. 10, 2022

(30) Foreign Application Priority Data

Jul. 31, 2019 (CN) .......................... 201910704057.2

(51) Int. Cl.
*A61B 3/00* (2006.01)
(52) U.S. Cl.
CPC ............ *A61B 3/0008* (2013.01); *A61B 3/005* (2013.01)
(58) Field of Classification Search
CPC ....... A61B 3/032; A61B 3/024; A61B 3/0025; A61B 3/0033; A61B 3/0058; A61B 3/02; A61B 3/028; A61B 3/0041; A61B 3/111; A61B 3/14; A61B 5/0022; A61B 3/103; A61B 3/113; A61B 3/1225; A61B 3/00; A61B 3/0325; A61B 3/036; A61B 3/1035; A61B 3/107; A61B 3/18; A61B 5/742; A61B 3/0083; A61B 3/0091; A61B 3/066; A61B 3/10; A61B 3/1015; A61B 3/12; A61B 5/0077; A61B 5/1071;
(Continued)

(56) References Cited

FOREIGN PATENT DOCUMENTS

| CN | 208591027 | * 3/2019 | ............. A61B 3/032 |
|---|---|---|---|
| JP | 3842975 | * 11/2006 | ............... A61B 3/02 |

(Continued)

*Primary Examiner* — Brandi N Thomas

(57) ABSTRACT

The invention provides a vision-testing method and vision-testing device. The vision-testing method is applied to the vision-testing device. The vision-testing device includes a light-transmitting apparatus, a plurality of vision test marks arranged on one side of the light-transmitting apparatus, and a plurality of light-emitting units arranged on another side of the light-transmitting apparatus for providing the vision test marks with a light source. The vision-testing method comprises the steps of obtaining a vision test command, controlling one of the light-emitting units to emit light according to the vision test command so as to highlight the corresponding vision test mark, obtaining user-response information and outputting a vision test result according to the user-response information and the highlighted vision test mark. The vision-testing method provided by the invention can achieve the vision test without a professional guidance, and the user can obtain real-time vision test information.

18 Claims, 5 Drawing Sheets

(58) Field of Classification Search
CPC .......... A61B 5/1172; A61B 5/12; A61B 5/16;
A61B 5/163; A61B 5/4088; A61B 5/411;
A61B 5/4839; A61B 5/4848; A61B
5/6803; A61B 5/6898; A61B 5/7405;
A61B 5/749; G02B 27/0075; G02B
30/10; G02B 27/0093; G02B 3/0056;
G02B 30/27; G02B 27/0025; G02B
30/30; G02B 30/50; G02B 2027/0116;
G02B 2027/0118; G02B 2027/0134;
G02B 2027/0138; G02B 2027/014; G02B
2027/0147; G02B 2027/0185; G02B
27/0172; G02B 7/14
See application file for complete search history.

(56) References Cited

FOREIGN PATENT DOCUMENTS

| | | | | |
|---|---|---|---|---|
| JP | 2019107455 | * | 7/2019 | ............. A61B 3/107 |
| WO | WO 2018069346 | * | 4/2018 | ........... G06T 7/0012 |
| WO | WO-2018069346 A1 | * | 4/2018 | ........... A61B 3/0008 |

* cited by examiner

VISION-TESTING METHOD AND DEVICE THEREOF

FIELD OF THE INVENTION

The invention relates to the technical field of a vision test, in particular to a vision-testing method and a device thereof.

BACKGROUND OF THE INVENTION

An eyeball is one of the most fragile organs in a human body, especially in the current era of information explosion and Internet+, human eyes are facing a great impact. There are many types of eye diseases, which are intricate, and once people suffer from the eye diseases, they are difficultly cured, but before the outbreak of the eye diseases, a sign will appear. Therefore, a timely test and a dynamic observation to eye vision are of great significance to the pre-control of the eye diseases.

At present, the main means of a vision test is still the traditional visual acuity chart. The visual acuity charts used in China include the International Standard Visual Chart, the logarithmic visual acuity charts and the Lang's round visual acuity charts, as well as some LED light box visual acuity charts. However, a problem confronts these visual acuity charts, which all need a professional to guide a vision test, especially for elimination to non-uniform factors such as light and distance, which cause problems such as inconvenience and inaccuracy in a vision test. For many people, it is not easy to get their own vision information conveniently. They need to go to a hospital or an eyeglasses store, there asking for such a guided test from a professional as to get their own vision information. In this era, it is extremely important for the people of the prevention and control of eye diseases to be able to obtain their own real-time vision information.

SUMMARY OF THE INVENTION

In order to overcome the problems in the prior art that a vision test requires a professional guidance and cannot obtain real-time vision information, a vision-testing method and a device thereof is provided for the purpose.

The invention provides a vision-testing method applied to a vision-testing device. Said vision-testing device includes a light-transmitting apparatus, a plurality of vision test marks arranged on one side of said light-transmitting apparatus, and a plurality of light-emitting units arranged on another side of said light-transmitting apparatus for providing said vision test marks with a light source. Said vision-testing method comprises the following steps:
  obtaining a vision test command;
  controlling one of said light-emitting units to emit light according to said vision test command so as to highlight and uniformly dispaly the corresponding vision test mark by said light-transmitting apparatus;
  obtaining user-response information;
  outputting a vision test result according to said user-response information and the highlighted vision test mark.

Further, said vision-testing method includes the following steps:
  obtaining user's location information and the luminance of said light-emitting unit;
  calculating an user's vision value according to said vision test result, said user's location information, the luminance of said vision test mark and the environmental brightness.

Further, said vision-testing method includes the following steps:
  obtaining user's account information and vision test time;
  associating said user's vision value and said vision test time with said user's account information and storing them.

Before the step of outputting a vision test result according to said user-response information and the highlighted vision test mark, said method further includes the following steps:
  judging whether said user-response information is consistent with preset response information;
  if said user-response information is consistent with said preset response information, controlling another light-emitting unit to emit light so as to highlight the corresponding vision test mark;
  if said user-response information isn't consistent with said preset response information, outputting a vision test result according to said user-response information and the highlighted vision test mark.

Further, said user-response information includes user's gesture information or face image information.

Further, said vision-testing method includes the following steps:
  obtaining an achromatopsia test command;
  controlling said light-emitting unit to display an achromatopsia test pattern according to said achromatopsia test command and a preset color temperature.

Further, said vision-testing method includes the following steps:
  obtaining an astigmatism test command;
  controlling said light-emitting unit to display an astigmatism test pattern according to said astigmatism test command and a preset light-emitting state.

Further, said vision-testing method includes the following steps:
  obtaining a vision-training command;
  controlling a plurality of said light-emitting units to emit light in sequence along a preset trajectory according to said vision-training command.

The invention further provides a vision-testing device, which includes a processor, a memory, a light-transmitting apparatus, a plurality of vision test marks arranged on one side of said light-transmitting apparatus, and a plurality of light-emitting units arranged on another side of said light-transmitting apparatus for providing said vision test marks with a light source. A vision test program is stored in said memory. Said vision test program is configured to be executed by said processor, and the above-mentioned method is implemented when said processor is executing said vision test program.

Further, said vision-testing device includes a light-emitting adjustment layer arranged between said light-transmitting apparatus and a plurality of said light-emitting units to adjust the brightness and uniformity of said vision text marks.

Compared with the prior art, the invention has the following beneficial effects: By obtaining the vision test command, one of the light-emitting units is controlled to emit light according to the vision test command, so that the corresponding vision test mark is highlighted, and the vision test result is output according to the user's response information to the highlighted vision test mark, so that the vision test can be completed without a professional guidance, and the user can obtain real-time vision test information. The invention also has functions as training vision and automatically collects user's training information, and the user can query and trace vision information and training information at any time to effectuate a mutual feedback effect for training and exercising vision.

DETAILED DESCRIPTION OF SOME EMBODIMENTS

We will further describe the invention as follows in combination with the drawings and embodiments. It should be noted that the following embodiments or technical features can be arbitrarily combined to form new embodiments, if not any conflict between them.

Figure 1:
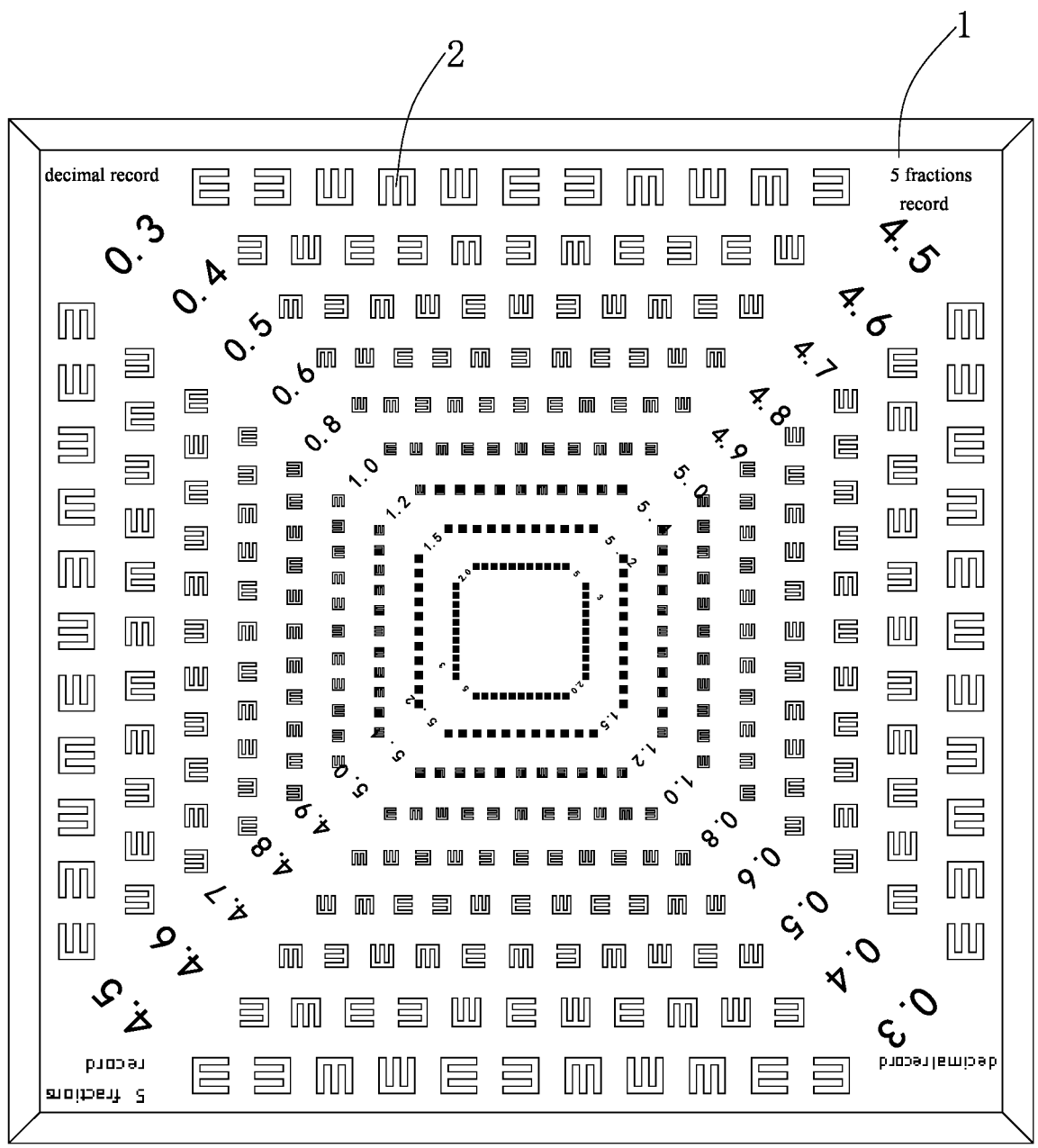
FIG. 1 is a schematic diagram of the vision-testing device provided by the embodiments of the invention.
Figure 2:
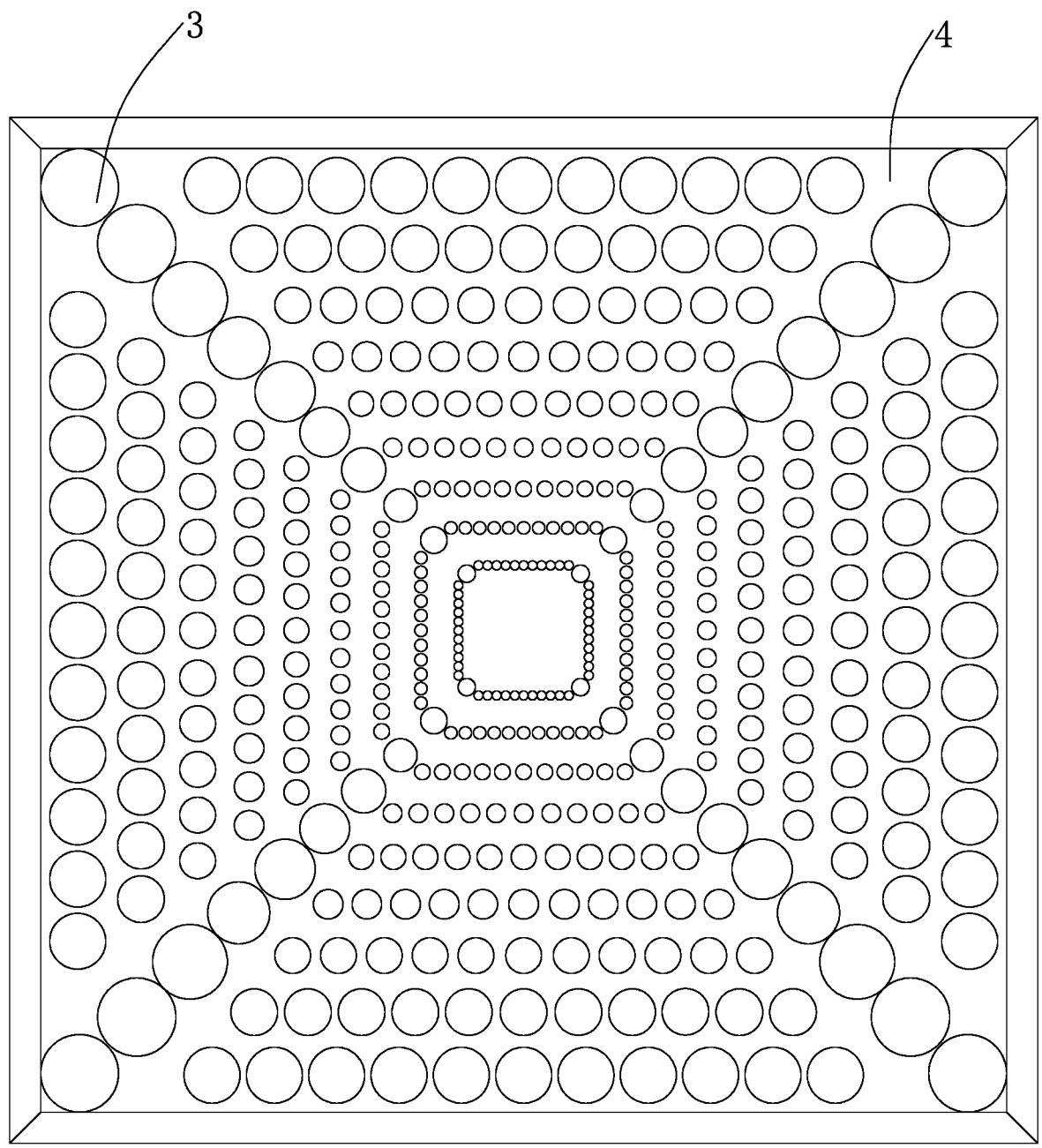
FIG. 2 is a schematic diagram of the arrangement of the light-emitting units of the vision-testing device provided by the embodiments of the invention.

As shown in FIGS. 1-2, The invention provides the vision-testing method applied to the vision-testing device. The vision-testing device includes the light-transmitting apparatus 1, a plurality of vision test marks 2 arranged on one side of said light-transmitting apparatus 1, and a plurality of light-emitting units 3 arranged on another side of said light-transmitting apparatus 1 for providing said vision test marks 2 with a light source, wherein the vision test marks 2 can be arranged as shown in FIG. 1, or in accordance with the standard logarithmic visual acuity chart or the Air Force C-shaped visual acuity chart. The light-emitting units 3 are arranged on a circuit board, and one light-emitting unit 3 may be composed of one LED lamp bead or a plurality of LED lamp beads. The light-emitting units 3 emit light according to the vision test command, so as to highlight the corresponding vision test mark 2, and the vision-testing device outputs the vision test result according to the user-response information, so as to achieve the vision test without a professional guidance. Furthermore, the vision-testing device can be placed in public places such as classrooms, libraries, subways, hospitals, etc., or in private places such as houses or offices, and can be hung on the wall or placed on the desktop, so that users can take a vision test whenever and wherever possible.

Further, the light-emitting units 3 may also display an achromatopsia test pattern, an achromatopsia correction pattern, an astigmatism test pattern, an astigmatism correction pattern, a myopia correction pattern, a hyperopia correction pattern, a glaucoma correction pattern, or a strabismus correction pattern, etc. according to the vision test command, so as to test the user's vision condition and correct the eyes. Compared with the paper pattern for achromatopsia or astigmatism test, the vision-testing device provided by the invention is more durable, and changeable in brightness of the pattern. The light-emitting units 3 can also emit light in sequence to form guiding spots according to a preset trajectory which are possibly a circle, an 8-shape, an inward or outward movement, a far and near straight line, a left and right line and the like. The user's eyes follow the light-emitting units 3 to complete eye muscle exercise. Users can choose the training mode according to their own situation. The device integrates a vision test and corresponding training to form a device for mutual feedback between vision screening and training, which can help users in discovering eye problems in time and training correspondingly, and which feeds back the effect of training to the user in time through the test function, and forms a timely interaction between a test and a treatment, so as to help users overcome the inertia of their own and eye movement, and realize the function of helping users exercise their eye muscles whenever and wherever possible. The users can test their eye diseases early and deal with them in time by themselves, instead delay until it is unable to improve condition, without a trouble to ask for such a guided treatment from a doctor.

In one embodiment, the vision-testing device also includes the light-emitting adjustment layer 4 arranged between the light-transmitting apparatus 1 and a plurality of light-emitting units 3, which may be a lens, a light filter, a light-guiding apparatus and the like. Further, the vision-testing device further includes the protective layer provided on the light-transmitting apparatus 1, such as light-transmitting PC material or tempered glass, performing the functions of softening light, homogenizing light and decorative effects, so as to improve comfort level of human eyes. In other embodiments, the light-transmitting apparatus 1 may also be made from light-transmitting PC material or tempered glass, performing the functions of softening light, separating light, homogenizing light and decorative effects by means of surface treatment technology.

Figure 3:
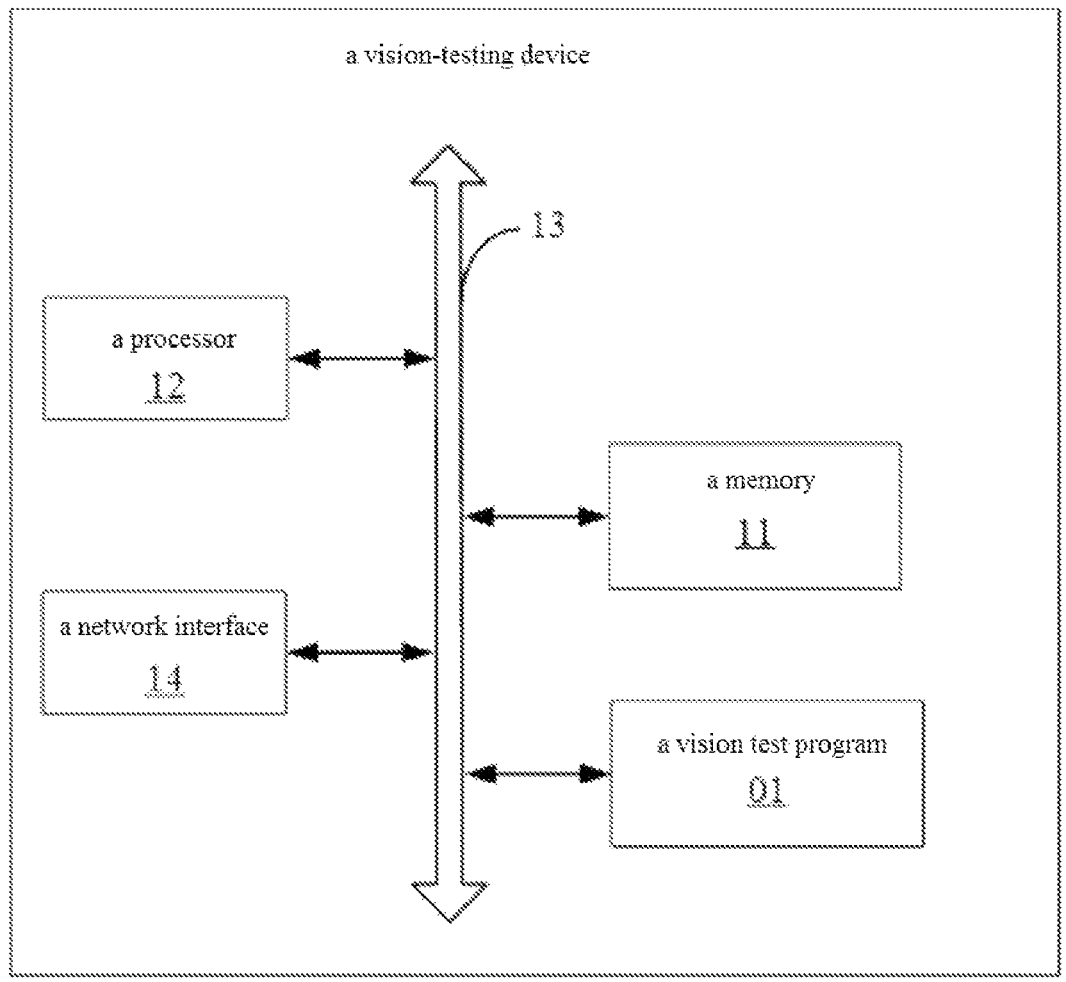
FIG. 3 is a schematic diagram of the internal structure of the vision-testing device provided by the embodiments of the invention.

FIG. 3 is a schematic diagram of the internal structure of the vision-testing device provided by the invention.

The vision-testing device at least includes the memory 11, the processor 12, the communication bus 13 and the network interface 14.

The memory 11 at least includes one type of readable storage mediums, which include a flash memory, a hard disk, a multimedia card, a card-type memory (for example, a SD or DX memory, etc.), a magnetic memory, a magnetic disk, an optical disk and the like. In some embodiments, the memory 11 may be an internal storage unit of the vision-testing device, such as a hard disk of the vision-testing device. In other embodiments, the memory 11 may also be an external storage device of the vision-testing device, such as a plug-in hard disk, a smart media card (SMC), and a secure digital (SD) card and a flash card and the like equipped on the vision-testing device. Further, the memory 11 may also include both the internal storage unit and the external storage device of the vision-testing device. The memory 11 can be used not only to store application software and various data installed in the vision-testing device, such as the code of the vision test program 01, but also to temporarily store data that has been output or will be output.

The processor 12 may be a central processing unit (CPU), a controller, a microcontroller, a microprocessor or other data-processing chips in some embodiments, used for running the program code stored in the memory 11 or processing data, such as executing the vision test program 01.

The bus 13 may be a peripheral component interconnect (PCI) bus or an extended industry standard architecture (EISA) bus or the like. The bus can be divided into an address bus, a data bus, a control bus and so on. To facilitate representation, only one thick line indicates the bus in the figure, but it does not mean that there is only one bus or one type of bus.

Further, the vision-testing device may also include the network interface 14, which may optionally include a wired interface and/or a wireless interface (such as a WI-FI interface, a Bluetooth interface). The network interface 14 is usually used for establishing the communication connection between the vision-testing device and other electronic devices.

FIG. 3 only shows the vision-testing device having the components 11-14 and the vision test program 01. It is obvious for a person skilled in the art that the structure shown in FIG. 3 does not limit the vision-testing device, and may include components fewer or more than those in the figure, or a combination of some components, or an arrangement of different components.

Figure 4:
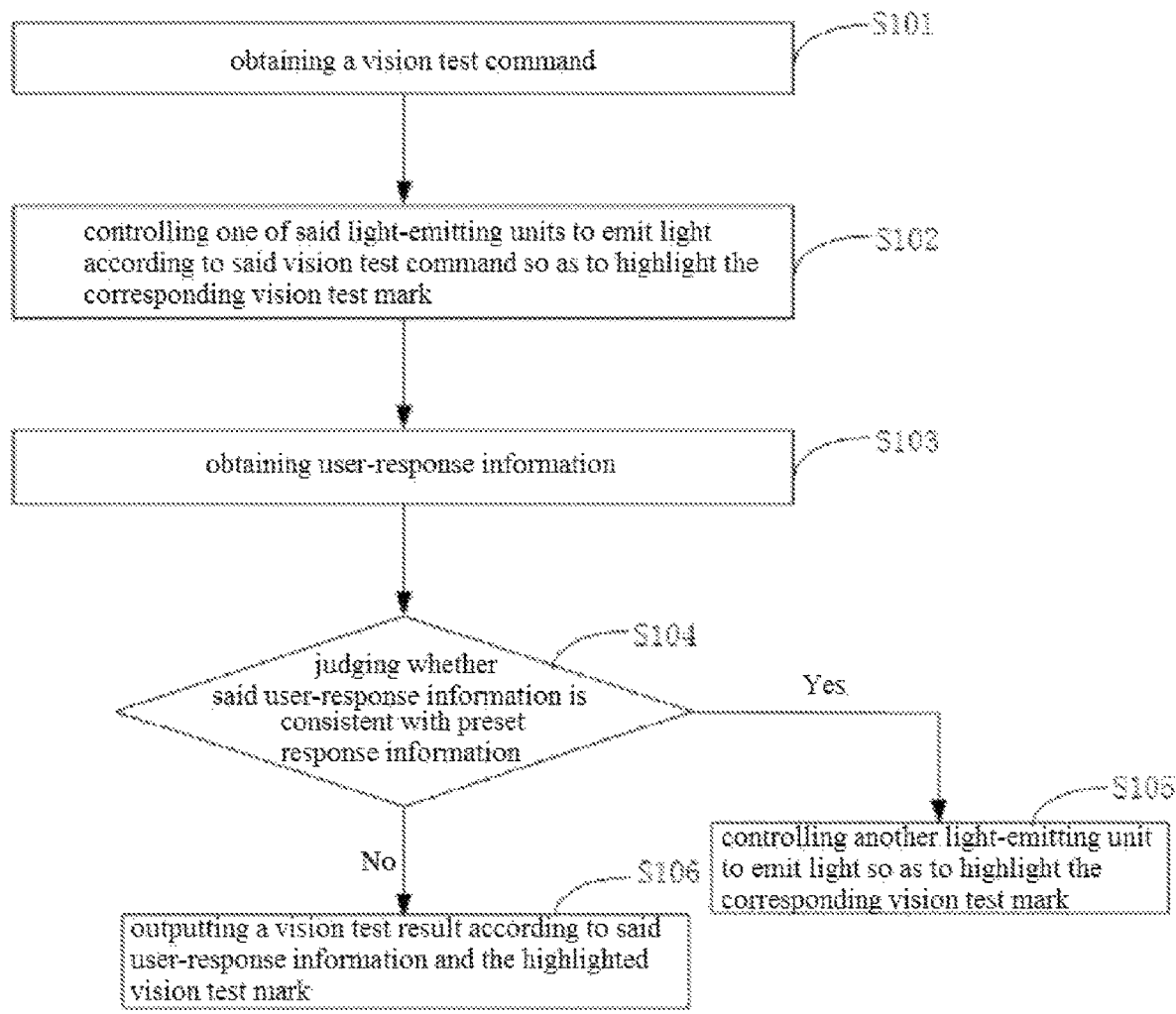
FIG. 4 is a flowchart of the vision-testing method provided by the first example of the invention.

As shown in FIG. 4, the vision-testing method provided by the first example of the invention includes the following steps:

S101: obtaining a vision test command.

Wherein, the vision test command can be activated by pushing a push-button provided on the vision-testing device, or the vision test command can be sent to the vision-testing device through a remote controller or a terminal communicating with the vision-testing device. Among them, the terminal may be, but is not limited to, a personal computer, a notebook computer, a smart phone, a tablet computer, and a portable wearable device.

S102: controlling one of the light-emitting units to emit light according to the vision test command, so as to highlight the corresponding vision test mark.

Specifically, when receiving the vision test command, the light-emitting unit corresponding to the outermost vision test mark emits light, or according to the vision value set by users, the vision test mark corresponding to the vision value is controlled to be highlighted.

In one embodiment, the LED-displayed information corresponding to the pattern to be displayed is stored in a FLASH in advance, after receiving the vision test command, according to the content to be displayed, a main control chip sends the corresponding LED-displayed information to a LED-driving chip. The LED-driving chip activates the corresponding LED lamp to display the corresponding patterns, and meanwhile controls the time and interval of lighting of the LED lamp. In one embodiment, the model of the main control chip is STM32F030CC6, and the model of the LED-driving chip is FZH182.

S103: obtaining user-response information.

The user-response information includes user's gesture information or face image information. In one embodiment, after the vision test mark is highlighted, the user stands at a preset position, then the device captures human body image information and extracts image features, comparing the extracted image features with pre-stored gesture features, so as to identify the gesture in the human body image information, such as up, down, left, or right. In another embodiment, after the vision test mark is highlighted, the user stands at a preset position, then the device captures face image information and detects the face, obtaining the center point of the left eye, the center point of the left eyeball, the center point of the right eye and the center point of the right eyeball, so as to calculate the rotation direction of the eyeballs.

S104: judging whether the user-response information is consistent with preset response information.

For example, if the "E" of the vision test marks currently highlighted faces upwards, the device judges whether the user's gesture or eye faces upwards as finally identified.

S105: If the user-response information is consistent with the preset response information, controlling another light-emitting unit to emit light so as to highlight the corresponding vision test mark.

Specifically, if said user-response information is consistent with the preset response information, it means that the user's eyes can clearly get the vision test mark currently highlighted, and then the device continues testing vision. For example, if the user identifies a vision test mark with a vision value of 0.6, the device highlights the light-emitting unit corresponding to the vision test mark with a vision value of 0.8 under control.

S106: If the user-response information isn't consistent with the preset response information, outputting a vision test result according to the user-response information and the highlighted vision test mark.

Specifically, if said user-response information isn't consistent with the preset response information, It means that the user cannot see clearly the vision test mark currently highlighted. For example, if the user can sequentially identify the vision test mark with a vision value of 0.6 and the vision test mark with a vision value of 0.8, when the user cannot identify the highlighted vision test mark with a vision value of 1.0, the user's vision value is 0.8.

In one embodiment, when the user takes a vision test, the device obtains the user's account information, for example, the user can log in by an ID card or through face recognition, and meanwhile obtain the time of the vision test. The device associates and stores the vision value, the vision test time, and the user's account detected each time to form a report, so as to facilitate users to view the information such as the frequency, date, and times of vision tests, in addition, the users can view the trend of vision changes so that they can trace their vision information.

In the vision-testing method provided by the above example, one of the light-emitting units is controlled to emit light according to the vision test command, so that the corresponding vision test mark is highlighted, and the vision test result is output according to the user-response information and the highlighted vision test mark, so that the vision test can be completed without a professional guidance, and a real-time vision test can be taken according to the method, which is convenient for users to use.

Figure 5:
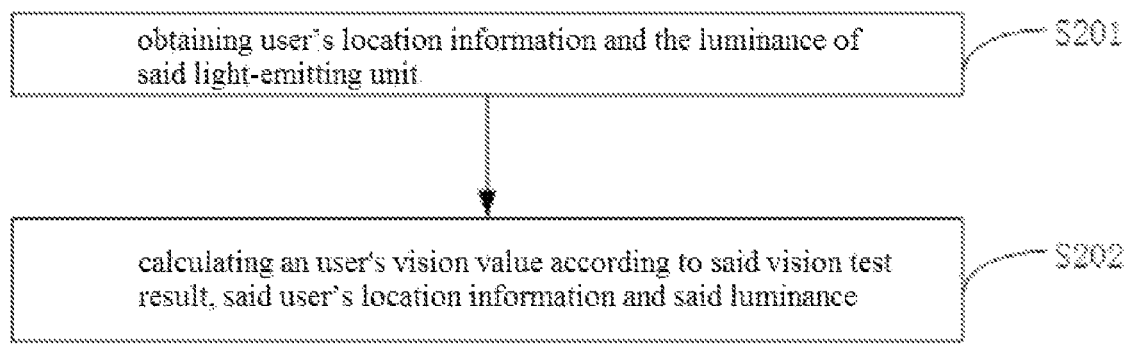
FIG. 5 is a flowchart of the vision-testing method provided by the second example of the invention.

As shown in FIG. 5, the vision-testing method provided by the embodiments of the invention differs from the first example in that it further includes:

S201: obtaining user's location information and the luminance of the light-emitting unit.

Specifically, when the user takes a vision test, the distance between the user and the vision test mark is calculated by means of infrared or radar, and the luminance of the current light-emitting unit is obtained at the same time.

S202: calculating an user's vision value according to the vision test result, the user's location information and the luminance.

Specifically, the user's actual vision value is calculated according to the vision test result, the user's location information, the luminance and the preset correspondence. For example, a plurality of users take a vision test with known vision values in advance, so as to establish a correspondence data table of the vision value, the user's location information, the luminance and the user's actual vision value detected by the vision-testing device. After testing vision, the use finds the actual vision value corresponding to the vision test result, the user's location information and the luminance form the data table.

In the above embodiment, the user can stand at any position in front of the vision-testing device to take a vision test, which is convenient for users to use.

In another embodiment, when obtaining the achromatopsia test command, the vision-testing device controls the light-emitting unit to display the achromatopsia test pattern according to the obtained achromatopsia test command and the preset color temperature. For example, the use can adjust the proportion of the three primary colors of RGB in the LED lamp bead to achieve different color temperatures and form an achromatopsia test pattern, so as to test whether the user has achromatopsia. When obtaining the achromatopsia correction command selected by the user, the device displays the corresponding achromatopsia correction pattern to correct the achromatopsia sufferer's vision.

In another embodiment, when obtaining the astigmatism test command, the vision-testing device controls the light-emitting unit to display the astigmatism test pattern according to the obtained astigmatism test command and the preset light-emitting state. For example, the device forms an astigmatism test pattern by adjusting the brightness of the LED lamp beads, so as to be able to test whether the user has astigmatism. When obtaining the astigmatism correction command selected by the user, the device displays the corresponding astigmatism correction pattern to correct the astigmatic patient's vision.

In another embodiment, when obtaining the vision-training command, the vision-testing device controls a plurality of light-emitting units to emit light in sequence along the preset trajectory according to the vision-training command, and the user's eyeball moves with the light-emitting unit to achieve the effect of training the eye muscles.

As known through the description in the above embodiments, a person skilled in the art can clearly understand that the invention can be implemented by means of software and a necessary common hardware platform. Based on this understanding, the technical solution of the invention in essence or its part involving an inventive step to the prior art can be embodied in the form of a software product. The invention also relates to computer-readable storage mediums, such as a ROM/RAM, a magnetic disk, an optical disk, etc., on which a computer program is stored, so the computer program is executed by a processor to implement the vision-testing method.

In the several embodiments provided in this application, it is obvious that the disclosed system, device and method may be implemented in other ways. For example, the embodiments of the device described above is only illustrative, as one instance, the unit is divided only as a logical function, there may be other division methods in actual implementation, as other instances, a plurality of units or components may be combined or integrated into another system, or some features can be ignored or not implemented. In addition, the mutual couplings or direct couplings or communication connections shown or discussed in the invention may be indirect couplings or communication connections between devices or units through some interfaces, which may be in electrical, mechanical or other forms.

It should be noted that the sequence numbers of the above-mentioned embodiments of the invention are only for description, and do not represent the superiority or inferiority of the embodiments. In addition, the terms "include", "comprise" or any other variants thereof in this application are intended to cover non-exclusive inclusion, so that a process, a device, a product or a method including a series of elements not only includes those elements, but also includes other elements that are not explicitly included or also includes the elements inherent to such a process, a device, a product or a method. In the case of no more limitations, the element defined by the sentence "including a . . . " does not exclude the existence of other identical elements in the process, the device, the product or the method that includes the element.

The above-mentioned embodiments are only preferred embodiments of the invention, and cannot be used to limit the protection scope of the invention. Any insubstantial changes and substitutions made by a person skilled in the art based on the invention pertain to the protection scope claimed by the invention.

What is claimed is:

1. A vision-testing method being applied to a vision-testing device, the vision-testing device comprising a light-transmitting apparatus, a plurality of vision test marks arranged on one side of said light-transmitting apparatus, and a plurality of light-emitting units arranged on another side of said light-transmitting apparatus for providing said vision test marks with a light source, wherein the plurality of vision test marks is arranged at multiple different subregions, and an arrangement of the vision test marks in each subregion comprises a plurality of rows or a plurality of columns; and in each subregion, the closer the row is to a center of the light-transmitting apparatus, the smaller the vision test marks corresponding to said row is; or the closer the column is to a center of the light-transmitting apparatus, the smaller the vision test marks corresponding to said column is, and wherein said method includes the following steps:

obtaining a vision test command;

controlling one of said light-emitting units to emit light according to said vision test command so as to highlight the corresponding vision test mark, wherein different vision test commands are configured to control light-emitting units at different positions to emit light, so as to highlight different vision test marks corresponding with the light-emitting units at different positions to display different patterns;

obtaining user-response information;

outputting a vision test result according to said user-response information and the highlighted vision test mark.

2. The vision-testing method according to claim 1, wherein said method further includes the following steps:

obtaining user's location information and the luminance of said light-emitting unit;

calculating an user's vision value according to said vision test result, said user's location information and said luminance.

3. The vision-testing method according to claim 2, wherein said method further includes the following steps:

obtaining user's account information and vision test time;

associating said user's vision value and said vision test time with said user's account information and storing them.

4. The vision-testing method according to claim 1, wherein before the step of outputting a vision test result according to said user-response information and the highlighted vision test mark, said method further includes the following steps:

judging whether said user-response information is consistent with preset response information;

if said user-response information is consistent with said preset response information, controlling another light-emitting unit to emit light so as to highlight the corresponding vision test mark;

if said user-response information isn't consistent with said preset response information, outputting a vision test result according to said user-response information and the highlighted vision test mark.

5. The vision-testing method according to claim 1, wherein said user-response information includes user's gesture information or face image information.

6. The vision-testing method according to claim 1, wherein said method further includes the following steps:
obtaining an achromatopsia test command;
controlling said light-emitting unit to display an achromatopsia test pattern according to said achromatopsia test command and a preset color temperature; wherein each of said light-emitting units comprises at least one LED lamp bead with three colors of Red, Green, Blue (RGB), and a proportion of the three colors of RGB is adjustable so as to achieve different color temperatures and form different achromatopsia test patterns.

7. The vision-testing method according to claim 1, wherein each of said light-emitting units comprises at least one LED lamp bead and brightness of the LED lamp beads of the light-emitting units is adjustable, and said method further includes the following steps:
obtaining an astigmatism test command;
controlling the light-emitting units to display an astigmatism test pattern by adjusting the brightness of the LED lamp beads according to said astigmatism test command and a preset light-emitting state.

8. The vision-testing method according to claim 1, wherein said method further includes the following steps:
obtaining a vision-training command;
controlling a plurality of said light-emitting unit to emit light in sequence along a preset trajectory according to said vision-training command.

9. A vision-testing device comprising a processor, a memory, a light-transmitting apparatus, a plurality of vision test marks arranged on one side of said light-transmitting apparatus, and a plurality of light-emitting units arranged on another side of said light-transmitting apparatus for providing said vision test marks with a light source, wherein a vision test program is stored in said memory, said vision test program is configured to be executed by said processor, and said method according to claim 1 is implemented when said processor is executing said vision test program;
wherein the plurality of vision test marks is arranged at multiple different subregions, and an arrangement of the vision test marks in each subregion comprises a plurality of rows or a plurality of columns; and
in each subregion, the closer the row is to a center of the light-transmitting apparatus, the smaller the vision test marks corresponding to said row is; or the closer the column is to a center of the light-transmitting apparatus, the smaller the vision test marks corresponding to said column is.

10. The vision-testing device according to claim 9, wherein said device includes a light-emitting adjustment layer arranged between said light-transmitting apparatus and a plurality of said light-emitting units, each of said light-emitting units comprising one LED lamp bead or a plurality of LED lamp beads.

11. The vision-testing device according to claim 9, wherein multiple visual values are provided between two adjacent subregions, each visual value corresponds to one row of the vision test marks in one of the two adjacent subregions and one column of the vision test marks in the other of the two adjacent subregions.

12. The vision-testing device according to claim 9, wherein the plurality of light-emitting units is arranged on different sub-position regions, an arrangement of light emitting units in each sub-position region comprises a plurality of rows and a plurality of columns; and
in each sub-position region, the smaller luminous area of the light emitting units indicated by the row closer to the center of the light-transmitting apparatus, or the smaller luminous area of the light emitting units indicated by the column closer to the center of the light-transmitting apparatus.

13. The vision-testing device according to claim 9, wherein the light-transmitting apparatus has a rectangular shape with two diagonal lines;
some of the light-emitting units are arranged along the two diagonal lines; and
the farther a distance between the light-emitting units arranged along the two diagonal lines and the center of the light-transmitting apparatus, the larger luminous areas of the light-emitting units is.

14. A vision-testing method being applied to a vision-testing device, the vision-testing device comprising a light-transmitting apparatus, a plurality of vision test marks arranged on one side of said light-transmitting apparatus, and a plurality of light-emitting units arranged on another side of said light-transmitting apparatus for providing said vision test marks with a light source, wherein the plurality of vision test marks is arranged at multiple different subregions, and an arrangement of the vision test marks in each subregion comprises a plurality of rows or a plurality of columns; and in each subregion, the closer the row is to a center of the light-transmitting apparatus, the smaller the vision test marks corresponding to said row is; or the closer the column is to a center of the light-transmitting apparatus, the smaller the vision test marks corresponding to said column is, and wherein said method includes the following steps:
obtaining a vision test command;
controlling one of said light-emitting units to emit light according to said vision test command so as to highlight the corresponding vision test mark,
obtaining user-response information;
outputting a vision test result according to said user-response information and the highlighted vision test mark;
wherein said method further includes the following steps:
obtaining a vision-training command;
controlling a plurality of said light-emitting units to emit light in sequence along a preset trajectory according to said vision-training command to thereby form guiding spots.

15. A vision-testing device comprising a processor, a memory, a light-transmitting apparatus, a plurality of vision test marks arranged on one side of said light-transmitting apparatus, and a plurality of light-emitting units arranged on another side of said light-transmitting apparatus corresponding to the vision test marks, wherein the plurality of vision test marks is arranged at multiple different subregions, and an arrangement of the vision test marks in each subregion comprises a plurality of rows or a plurality of columns; and
in each subregion, the closer the row is to a center of the light-transmitting apparatus, the smaller the vision test marks corresponding to said row is; or the closer the column is to a center of the light-transmitting apparatus, the smaller the vision test marks corresponding to said column is, and wherein a program is stored in said memory and configured to be executed by said processor to perform following steps:

obtaining a vision-training command;

controlling a plurality of said light-emitting units to emit light in sequence along a preset trajectory according to said vision-training command to form guiding spots such that user's eyeball can move following with the guiding spots to do eye muscle exercise.

16. The vision-testing device of claim 15, wherein the preset trajectory comprises at least one of the following:

a circle trajectory;

an 8-shaped trajectory;

a straight-line movement trajectory; and an inward or outward movement trajectory.

17. The vision-testing device of claim 15, further comprising a plurality of numbers arranged on the one side of said light-transmitting apparatus corresponding to the vision test marks for denoting vision value of the corresponding vision test marks.

18. The vision-testing device of claim 15, wherein the light-emitting units correspond to the vision test marks in a one-to-one correspondence;

the smaller the vision test mark, the smaller the area of the corresponding light-emitting unit; and the larger the vision test mark, the larger the area of the light-emitting unit.

\* \* \* \* \*